United States Patent [19]

Gancy

[11] 4,377,488

[45] Mar. 22, 1983

[54] PROCESS OF MAKING CALCIUM ACETATE DEICING AGENTS

[76] Inventor: Alan B. Gancy, 265 Robineau Rd., Syracuse, N.Y. 13207

[21] Appl. No.: 333,037

[22] Filed: Dec. 21, 1981

[51] Int. Cl.$^3$ .................... C09K 3/18; C07C 51/41; C01F 11/00

[52] U.S. Cl. .................................. 252/70; 252/381; 252/385; 252/387; 562/607; 562/608; 423/169; 423/173; 423/155; 423/430; 423/438; 423/637; 423/641; 106/13

[58] Field of Search .............. 252/70, 381, 385, 387; 562/607, 608; 423/169, 173, 155, 430, 438, 637, 641; 106/13

[56] References Cited

U.S. PATENT DOCUMENTS 4,239,736 12/1980 Fenske ............................ 423/173

Primary Examiner—John E. Kittle
Assistant Examiner—Robert A. Wax
Attorney, Agent, or Firm—Austin R. Miller

[57] ABSTRACT

A process of making a calcium acetate-containing solution having a pH value at room temperature between about 7 and about 8 is provided comprising reacting acetic acid with a carbonate compound, adding calcined limestone, and optionally finishing off the acid-base reaction with an amount of an alkali metal hydroxide comprising from about 2% to about 5% of the total stoichiometric complement to the amount of acetic acid. Further process options which may be used in the preparation of deicing agents include adding coarse limestone to the above-prepared calcium acetate-containing solution in amounts up to 10% by weight and converting the solution into solid flakes.

5 Claims, No Drawings

PROCESS OF MAKING CALCIUM ACETATE DEICING AGENTS

The subject matter of the present invention is related to the subject matter of my two copending applications, Ser. Nos. 316,816 and 319,473.

BACKGROUND OF THE INVENTION

The present invention relates to methods of manufacturing novel deicing agents and more specifically relates to processes of making calcium acetate and calcium magnesium acetate salts to be used in applications such as road deicing for example.

DESCRIPTION OF THE PRIOR ART

U.S. Pat. Nos. 3,624,243 and 3,630,913, granted to Scott, Jr. et al both relate to chemical deicers containing magnesium and aluminum corrosion inhibitors making them especially suited for use on airport runways. Scott teaches the use of solutions containing urea, ethylene glycol, ammonium nitrate and water soluble chromate salts.

U.S. Pat. No. 4,163,079, granted to Beafore, teaches the spraying of belt transportation surfaces with a composition consisting of a water soluble polyhydroxide compound or a monoalkyl ether, and a water soluble organic compound having at least one hydrophilic group.

U.S. Pat. No. 4,254,166, granted to Glanville et al, discloses a composition for reducing the strength of ice consisting of from 5-90 wt. % of a water soluble organic compound selected from the group consisting of alkynols, diols, polyols, ketones, ethers, carboxylics acids and mixtures thereof; and from 1-20 wt. % of a substance containing ammonium ions selected from the group consisting of ammonium acetate, ammonium nitrate, ammonium sulphate, ammonium sulfamate, ammonium formate, ammonium cyanate, ammonium thiocyanate, ammonium carbonate, ammonium pentaborate, and mixtures thereof.

U.S. Pat. No. to Budenholzer et al, 2,918,052, teaches the use of metallic sodium and caustic (NaOH) formed in the reaction of sodium and water, as a deicing agent. The exothermic nature of the sodium and water reaction, together with the freezing point depressant effect exerted by the caustic, results in a dual action deicing agent.

U.S. Pat. No. 4,081,256, granted to Donnelly, discloses a particulate composition which undergoes an endothermic reaction when mixed with water. This composition consists of urea, hydrated sodium acetate, potassium chloride or potassium nitrate, ammonium chloride and quar gum. Donnelly teaches the use of hydrated sodium acetate in applications requiring a reduction in temperature.

Sodium chloride and calcium chloride are the most common road deicing agents in use today. Sodium chloride is somewhat less expensive due to its high deicing efficiency and the wide distribution of natural deposits in the United States. Sodium chloride occurs naturally in a substantially pure state and hence needs only to be mined and ground to the appropriate particle size for storage, shipment and use.

Large quantities of calcium chloride are produced as a co-product of the well known Solvay Process for manufacturing sodium carbonate.

Because sodium chloride and calcium chloride are nominally the least expensive road deicing salts, they are the most widely used road deicers in the United States. Annual use of sodium chloride for road deicing in the U.S. exceeds 9,000,000 tons.

Unfortunately, it has recently come to light through environmental studies that the costs of buying and applying sodium chloride and calcium chloride road deicers are misleading indices of the total cost of using these deicing agents. It has been estimated that damage to vehicles and highway structures through corrosion, and damage to flora, fauna and water supplies inflates the true cost to 14-22 times the nominal cost of manufacturing sodium chloride salt.

Thus, there has been a keen need in the road deicing field for a cheap and environmentally safe road deicing agent. One end result of this effort culminated in a report by Bjorksten Research Laboratories (BRL) which developed a calcium magnesium acetate salt as a substitute for NaCl.

BRL conducted so-called wet/dry testing of homemade concrete slabs. They used one-half saturated and one-quarter saturated CMA solutions. BRL's CMA salt was an equimolar mixture of CA and MA, and had the following formula:

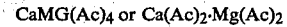

$CaMG(Ac)_4$ or $Ca(Ac)_2 \cdot Mg(Ac)_2$

Unfortunately, the Bjorksten work ended in seeming failure because of the propensity of their calcium acetate salts to attack portland cement concrete. Thus, there has been a further strong need in the art for a substitute deicing agent, such as calcium acetate, which does not exhibit the potentially harmful scaling properties of the calcium acetate salt developed by Bjorksten Research Laboratories.

There has been a further need in the art for a low cost method of producing a deicing agent to make it more economically attractive as a substitute for sodium chloride.

Calcium acetate (CA) and calcium magnesium acetate (CMA) meet the requirements for safe, non-polluting road and highway deicing agents in most respects. However, they are inherently more costly than salt or calcium chloride. When CA and CMA are prepared by straightforward neutralization of acetic acid by the appropriate calcium base, the predominant cost factor is the relatively high cost of the raw material acetic acid. Any commercial development plans would therefore have to include a search for the cheapest available source of acid, such as industrial waste streams, for example.

And whereas acid raw material cost is the prime economic target in a successful commercialization venture, other manufacturing costs must be examined carefully in order to make CA and CMA as competitive as possible with existing deicers. From what has already been stated, CA does not have to cost less than or equal to salt in order for it to be attractive. Instead, the total societal cost of using CA must be less than the total societal cost of using salt or calcium chloride. If government figures are correct, CA can cost 14 to 22 times more than salt and society would still "break even." On a more realistic plane, society must really "come out ahead" through use of CA instead of salt. In that event, cost of CA and its application can be as much as, say, seven times that of salt.

Other processes have been proposed which promise low-cost CA and CMA product. Among these are the synthesis of CA/CMA from cellulose and/or from wood. These favorable cost estimates are based on the availability of low-cost cellulose or wood raw materials derived from municipal solid wastes. The feasibility of using solid waste raw materials remains questionable. Besides, the chemistry and chemical engineering involved have not yet been developed. Even if successful, the solid wastes approach is many years away from commercial realization.

Neutralization processes are the most likely to have success in the short-term approach to new CA and CMA deicers. I have discovered neutralization process improvements which reduce investment costs as well as manufacturing costs. And, while it is recognized that acid raw material cost is a more worthwhile target, it can be argued that especially in view of such high acid costs, all other costs associated with CA manufacture should be minimized if possible. The present invention addresses itself to those other costs.

Specifically, I have discovered an effective means of utilizing cheap limestone with only supplemental use of the more costly lime (calcined limestone) in the manufacture of CA and CMA.

Lime is produced from limestone by a high temperature, energy-intensive calcination process. Hence, lime costs substantially more than limestone. But variable cost is not the only cost consideration. In the event that the CA/CMA market opens up it is probable, at least on a geographically-localized basis, that additional lime production capacity will be needed. Such added capacity will necessitate new large-scale capital investment which may present a serious economic roadblock to CA/CMA development. The building of new capacity automatically elevates the price of lime. In addition to variable costs there will be the added burden of paying off the investment, both of which are reflected in the price of lime produced from expanded (or new) lime plant facilities.

Hence it is desirable to use as much of the cheaper limestone as CA/CMA raw material as possible. It is generally recognized by those skilled in the art that lime will be a good candidate raw material in the neutralization of acetic acid to make CA. However, even this apparently straightforward process is not without its complications. However, I will focus for the moment on limestone, or the chemically-purified form of limestone, calcium carbonate.

It is worth mentioning at this point that limestone contains varying amounts of magnesium, depending upon the mineral source. This magnesium is manifest as dolomite (hence "dolomitic limestone") which is unreactive to acetic acid. Only when the dolomitic limestone is calcined to lime does this magnesium become reactive as is taught in my co-pending application, Ser. No. 316,816. Hence, magnesium acetate (MA) will be a co-product with calcium acetate (CA) to the extent that magnesium is present in the calcined limestone used to supplement limestone in my novel processes. But MA is known to be a superior deicer to CA. Hence, the presence of MA is desirable, for deicing purposes, in the mixed product I call CMA.

With regards to other components of natural limestone, use of uncalcined natural mineral limestone as a major raw material in the process of my invention poses no known detriments, unlike the use of calcined limestone. On the contrary, a certain fraction of available calcium base is rendered chemically inactive, or unusable, when limestone is calcined. This material is known as "over-burned" or "dead-burned" lime. This material is unuseable and represents inefficient use of limestone. I will describe later in this application, however, a means of turning even this apparent disadvantage into a surprising product-improvement feature.

Previous workers reacted calcium carbonate with acetic acid such that the system was allowed to equilibrate in the presence of excess calcium carbonate. This resulting solution phase contained CA and an inevitable excess of acetic acid. This solution, even when boiled down and dried at elevated temperature, led to a solid in which molecular acetic acid was stubbornly attached to CA.

In CA and CMA deicer synthesis, the presence of excess acetic acid in the product is highly undesirable for at least three reasons:

(1) Acetic acid is a poor deicer;

(2) Acetic acid in the final product represents a waste of expensive raw material, and (3) A certain amount of excess acid in CA will be present in its molecular, or undissociated form. It is the latter which is known to be a rather universal and powerful solvent. The presence of such undissociated acid could be detrimental in CA end-use applications in terms of attack on materials of construction.

It should be appreciated that in the road deicing applications, the objective is not always to melt all the ice or snow. This would require mammoth amounts of deicer. The objective is to effectively melt snow or ice on a very localized basis so as to "drill holes" in the ice, down to the pavement. Then, under the impact of vehicular traffic, these "holes" give rise to connecting cracks which subsequently dislodge large chunks of ice and snow from the roadbed.

It is clear, then, that a fine granulated powder deicer would be relatively ineffective under the above conditions. The powdered deicer would be wasted through application of much too heavy a dose. Large, spherulitic granules are better for concentrating the deicer into localized spots. However, on hard surfaces, these spheres tend to "bounce" and resist uniform distribution during application.

Thus, a preferred form of deicer is the flake. The ideal size CA flake is about 1/16 inch average thickness and about ½ inch average "diameter".

OBJECTS OF THE INVENTION

Thus, it is an important object of the present invention to provide an environmentally safe, inexpensive substitute road deicing agent for salts such as sodium chloride and calcium chloride.

It is an important object of this invention to reduce the cost of manufacturing elements, other than the cost of raw material acetic acid, in the manufacture of non-polluting CA and CMA deicers.

It is another important object of the present invention to provide a deicing agent which inhibits corrosion.

It is a still further object of the present invention to provide such a deicing agent which does not attack portland cement concrete.

SUMMARY OF THE INVENTION

A process of making a calcium acetate-containing solution having a pH value at room temperature between about 7 and about 8 comprises reacting acetic acid with a carbonate compound, adding calcined limestone, and optionally finishing off the acid-base reaction with an amount of an alkali metal hydroxide comprising from about 2% to about 5% of the total stoichiometric complement to the amount of said acetic acid. Further process options to be used in the preparation of deicing agents include adding coarse limestone to the above-prepared calcium acetate containing solution in amounts up to 10% by weight of the deicing agent and converting the calcium acetate-containing solution into solid flakes for deicing applications.

DESCRIPTION OF THE PREFERRED EMBODIMENTS

I have discovered that when a large excess of acid with respect to calcium carbonate is used, complete reaction of the calcium carbonate ensues. In the case of chemically-pure calcium carbonate, it dissolves completely, leaving no residue. When at least 43 percent excess (over and above the theoretical stoichiometric amount) acetic acid is used, all of the calcium carbonate reacts. I refer here to industrial-strength solutions, i.e. of a strength such that the final product CA liquor is close to its solubility limit. The purpose in using strong solutions is to minimize water-evaporation costs during production of a solid CA product.

In other words, up to 70 percent of the calcium base required to produce CA can be in the form of active calcium carbonate. The remainder of the required base, as shown in my experiments, can be lime, or the active $Ca(OH)_2$ content of slaked calcined limestone.

Thus the total complement of acid is first reacted with 70 percent of the required base in the form of finely divided limestone, until the reaction is completed. To this product is added 30 percent of the required base in the form of calcined limestone. This produces the desired near-saturated solution of CA. The solution will contain impurities, most of which are insoluble. After careful adjustment of the final end-point the solid impurities are (optionally) retained, and the resultant CA slurry is ready for use as such. Preferably, however, it is dried to a solid product. Both the end-point adjustment and the handling of insoluble solids constitute important features of my invention, and are discussed in further detail. Further, the physical form of my CA/CMA products is important, as is discussed in further detail.

The limestone is preferably finely ground in order to achieve a reasonably short reaction time. I have discovered that ordinary stirring of the reaction batch is ineffectual. Complete reaction during stirring requires in excess of three hours, even for small batches. A heavy sludge forms which is difficult to handle. On the other hand, I have found that a highly agitated reactor reduces the complete reaction time to less than 30 minutes. I used a Waring blender as a laboratory reactor. The shearing action of such agitation obviates the gas-binding inhibition due to product carbon dioxide and the sludge is effectively broken up.

Even with the Waring blender, large evolving gas bubbles form in the vortex of the blender, and are stabilized by the sludge present. I have discovered that if acetic acid is added to a water slurry of limestone, this sludge or froth is destroyed. As the acid is slowly introduced into the vortex, the foam is destabilized by the fresh incoming acid.

Thus I have found it preferable to add acid to base, rather than the reverse. This has an additional benefit of reducing losses of acetic acid, thereby improving industrial hygiene. The reactor is inevitably warm, both from the positive heat of reaction, and from the energy introduced through the high-speed agitation. If the acid were added to the reactor first, then the base added piecemeal, acid volatility would pose more of a problem. By the use of my method, there is virtually no unreacted acid present in the early stages of the reaction, at least. Later on, of course, we deliberately have a large excess of acid present to assure complete dissolution of active calcium carbonate. But then this excess is subsequently neutralized by incoming lime.

In the event that an unusually plentiful and cheap source of lime, or calcined limestone, is available, then lime alone may be used as the calcium base. As earlier stated, such use would seem to be obvious to those skilled in the art. However, I have discovered that the reaction between acetic acid and calcined lime at industrial concentrations is complex and does not proceed according to textbook models. In particular, the neutralization end-point is complex. Unless handled properly, the system ends up too far on the acidic side, or too much on the basic side. If too acidic, there is an objectionable amount of undissociated acetic acid in solution, with the undesirable consequences discussed earlier. If too basic, there is the undesirable consequence of adding high levels of a "caustic" product to the environment.

Note that this end-point problem exists whether lime comprises 100 percent of the calcium base, or only 30 percent as in the above-described method. Hence, proper use of lime is not necessarily obvious, especially as concerns consequences to the product, and ultimately, to the environment.

The pH of a calcium acetate solution at room temperature is known to be 7.6. It is the salt formed by the union of a weak acid and a strong base. Hence upon hydrolysis in water CA is alkaline rather than acidic in nature. A pH greater than 7.0 signifies by convention an alkaline system.

Therefore, the end point of the reaction of acetic acid and calcium hydroxide (calcined limestone, slaked) should be close to 7.6. I say "close to" because each and every one of the manifold impurities in natural limestone contribute to the final pH of the liquor. Besides, magnesium acetate could conceivably constitute up to 50 mol percent of the product, and the CA/MA combination would in all probability have a pH which is not exactly 7.6.

As was mentioned above, there is a serious concern over the undissociated acetic acid content in the CA/CMA product. The reason that this species can exist at such relatively high levels is that the solution contains a high level of acetate ion deriving from the product, CA. This acetate level causes a suppression of acetic acid dissociation. It "drives the written reaction in reverse":

| undissociated | hydrogen | acetate |
| acetic acid | ion | ion |

An understanding of undissociated acid levels may be gained from the following (approximate) values of the $HAc/Ac^-$ concentration ratio at differing pH levels (at room temperature):

| pH | HAc/Ac⁻ Concentration Ratio |
|---|---|
| 5 | 0.6 |
| 6 | 0.06 |
| 7 | 0.006 |
| 8 | 0.0006 |
| 9 | 0.00006 |

Thus, at pH 6 the level of undissociated acid is an appreciable 5.7 percent of the total of acetic species. At pH 7 it is 0.6 percent, etc.

Thus, I have found that it is preferable to set the desired reaction endpoint between pH 7.0 and 8.0. Although respected authorities teach the simple weighing out of the required ingredients and carrying out the batch reaction in order to reach the desired pH, I have found that the reaction mechanisms are not so simple in practice.

Consider first of all the impurities in slaked calcined limestone. There are, of course, components such as sand and other relatively unreactive siliceous materials. In addition, there may also be unslaked lime, or CaO. This is important in that it makes the base stronger, weight for weight, than the theoretical 100 percent $Ca(OH)_2$ would be. Then there is "dead-burned" lime which may be relatively unreactive to acetic acid even though it gives a more correct titre with hydrochloric acid.

Still further, there may be other impurities in the lime, the acid and the water which lead to insoluble precipitates at the end-point pH. For example, even when using analytical grade reactants a tan flocculent precipate forms near the end-point which obscures the end-point if one is using the visual criterion of complete disappearance of all the solid $Ca(OH)_2$. When tap water is used, the amount and color of this precipitate intensifies. Hence, ferric hydroxide (or some other basic ferric salt) is either present to begin with, or is formed from a source of ferric ion during the synthesis of CA. The fact of this precipitation is the basis for a CA purification scheme which I propose, in the event that CA is manufactured for purposes, other than deicing, where high purity may be desired. It is simply to filter the slurry to remove these undesirable impurities.

Now consider reaction kinetics at a point approaching the end-point from either direction. For example, when $Ca(OH)_2$ is added to acetic solution, even when using carefully measured analytical grade materials, I have discovered appreciable solid residues when only about 96 percent of the $Ca(OH)_2$ has been added to the acid. This indicates that the attack of $Ca(OH)_2$ by hydrogen ions is very slow at this point. Hence, the reaction is in pseudoequilibrium wherein unreacted acid and base are present in the same solution. Thus, the reaction mixture contains a relatively high level of the unwanted undissociated HAc, for example at pH 6, even though there is apparently more than enough base present to neutralize it.

Although the simple solution to this problem would seem to be adding more $Ca(OH)_2$, I found that it is difficult to control the quantities. As a result, the pH typically jumps to 9.8. This is close to the pH of pure $Ca(OH)_2$ suspended in water. The pH is now too high, not because we've completely formed CA by utilization of acid, but because $Ca(OH)_2$ is supplying hydroxyl ions to the pseudoequilibrium system. As shown above, a highly alkaline product is as undesirable as a highly acidic one.

Looking at kinetics from another view, near the endpoint one is trying to react a very low hydrogen ion concentration ($10^{-6}$) with a $Ca(OH)_2$ surface in a strong solution of CA. For one thing, the solubility of $Ca(OH)_2$ is expected to be depressed due to the high concentration of calcium ion in solution. For example, there may be absorption effects which slow down $Ca(OH)_2$ surface reactions. The ionic strength of such a system is also high, and one can only guess at the effect this may have on the kinetics.

It may be argued that the pH 9.8 system could be back-titrated with acid to the desired end-point pH. However, in order to do this it is necessary to first remove all solids by filtration. Otherwise, the "endpoint" pH drifts back up again due to slow reaction of the basic solids downstream in the process. Unfortunately, this filtration step adds another costly step to the operation. However, certain insoluble solids in the final product are not only harmless, but are actually desirable in deicer product applications. These solids include sand, siliceous matter, dead-burned lime, basic iron compounds, and perhaps some calcium carbonate resulting from exposure of lime to atmospheric $CO_2$. These insoluble solids in deicers have the desirable effect of improving vehicular traction on roads and highways.

To summarize, it is desirable to reach the final endpoint through use of calcined limestone base, regardless of the order of addition of acid and base. On the one hand a safe "real" equilibrium deficiency of base allows undissociated acid to reach dangerously high levels. On the other, an excess of base, even properly back-titrated, leads to pH drift and an over-alkaline product. To obviate the latter problem, a costly filtration step is required.

I have discovered a practical solution to the above problem. It is simply to add enough slaked calcined limestone to the acid to bring the pH to a steady value of around 6. At this point there will undoubtedly be a number of solid species present. Then I add a solution of potassium hydroxide to bring the pH up to a value between about 7 and about 8. Sodium hydroxide may also be used, but from an environmental pollution standpoint, the potassium hydroxide base is preferred.

Furthermore, I propose to take advantage of the favorable effects of solids inclusion by eliminating the liquor filtration step which normally follows a chemical synthesis. Furthermore, I have discovered that the addition of calcium carbonate to the final process liquor does not alter the pH of the system.

Thus, approximately 95 percent of the required base comprises (impure)calcium hydroxide. The other 5 percent comprises KOH. Hence, the product will not be, strictly speaking, calcium acetate, but will contain some potassium acetate which is also an effective deicer. Potassium acetate is also harmless to the environment. Potassium is a major component of agricultural fertilizers. It also helps to balance off the sodium ion levels in ground waters. The biodegradation product of potassium acetate would be potassium carbonate, an environmentally harmless substance.

Although carbonates can also be used as complementary bases in the synthesis, they are less desirable due to the formation of insoluble $CaCO_3$ at reaction interfaces.

Although this invention has been described in connection with specific forms thereof, it will be appreciated by those skilled in the art that a wide variety of equivalents may be substituted for those specific elements and steps of operation shown and described herein, that certain features may be used independently of other features, and that parts may be reversed, all without departing from the spirit and scope of this invention as defined in the appended claims.

I claim:

1. In a process of making a calcium acetate-containing solution having a pH value at room temperature in the range from about 7 to about 8, the steps comprising:
   a. reacting acetic acid and an amount of calcined limestone comprising about 95% to about 98% of the total stoichiometric complement of said acetic acid; and
   b. adding an alkali metal hydroxide in an amount comprising from about 2% to about 5% of said total stoichiometric complement.

2. In a process of making a calcium acetate-containing solution having a pH value at room temperature in the range from about 7 to about 8, the steps comprising:
   a. completely reacting a carbonate with acetic acid, wherein the amount of said carbonate comprises from about 50% to about 70% of the total stoichiometric complement of said acid;
   b. adding calcined limestone in an amount comprising from about 25% to about 50% of said total stoichiometric complement; and
   c. adding an alkali metal hydroxide in an amount comprising from about 2% to about 5% of said total stoichiometric complement.

3. In a process of making a calcium-acetate containing deicing agent, the steps comprising:
   a. adding coarse limestone to a calcium acetate-containing solution;
   b. agitating the calcium acetate-coarse limestone suspension; and
   c. converting said suspension into a substantially solid deicing agent.

4. The process as defined in claim 3, wherein said coarse limestone comprises up to about 10% by weight of said deicing agent.

5. In a process of making calcium acetate-containing solid flakes, the steps comprising:
   a. removing water from a substantially saturated calcium acetate-containing solution by heating the solution to form a solid calcium acetate-containing product.

* * * * *

UNITED STATES PATENT AND TRADEMARK OFFICE
CERTIFICATE OF CORRECTION

PATENT NO. : 4,377,488
DATED : March 22, 1983
INVENTOR(S) : Alan B. Gancy

It is certified that error appears in the above-identified patent and that said Letters Patent is hereby corrected as shown below:

Column 2, line 27, delete "CaMG" and insert --CaMg--.

Signed and Sealed this

Nineteenth Day of July 1983

[SEAL]

Attest:

GERALD J. MOSSINGHOFF

Attesting Officer

Commissioner of Patents and Trademarks